US011029307B2

(12) United States Patent
Benson

(10) Patent No.: US 11,029,307 B2
(45) Date of Patent: Jun. 8, 2021

(54) APPARATUS FOR MONITORING BLOOD COAGULATION

(71) Applicant: Benson Viscometers Ltd., Kilgetty (GB)

(72) Inventor: Charles Bernard Benson, Kilgetty (GB)

(73) Assignee: BENSON VISCOMETERS LTD, Kilgetty (GB)

( * ) Notice: Subject to any disclaimer, the term of this patent is extended or adjusted under 35 U.S.C. 154(b) by 938 days.

(21) Appl. No.: 15/514,356

(22) PCT Filed: Sep. 25, 2015

(86) PCT No.: PCT/GB2015/052782
§ 371 (c)(1),
(2) Date: Mar. 24, 2017

(87) PCT Pub. No.: WO2016/046565
PCT Pub. Date: Mar. 31, 2016

(65) Prior Publication Data
US 2017/0292941 A1    Oct. 12, 2017

(30) Foreign Application Priority Data
Sep. 25, 2014    (GB) .................................... 1416944

(51) Int. Cl.
*G01N 33/49*    (2006.01)
*G01N 27/06*    (2006.01)
(52) U.S. Cl.
CPC ......... *G01N 33/4905* (2013.01); *G01N 27/06* (2013.01); *G01N 33/49* (2013.01)

(58) Field of Classification Search
CPC ......... G01N 33/49–4925; G01N 27/04; G01N 27/06–10
See application file for complete search history.

(56) References Cited

U.S. PATENT DOCUMENTS

| 4,869,812 A | * | 9/1989 | Schoendorfer | ........ B01D 61/08 |
| | | | | 210/321.63 |
| 5,603,845 A | * | 2/1997 | Holm | ........................ B04B 7/00 |
| | | | | 210/782 |
| 2003/0029254 A1 | * | 2/2003 | Hvidtfeldt | ........... B01F 11/0017 |
| | | | | 73/863.33 |

(Continued)

FOREIGN PATENT DOCUMENTS

| EP | 3198273 B1 | 9/2019 |
| GB | 1322412 | 12/1973 |

(Continued)

OTHER PUBLICATIONS

Examination Report from the United Kingdom Intellectual Property Office for Application No. GB1516958.4, dated Oct. 31, 2019, 7 pages.

*Primary Examiner* — Huy Q Phan
*Assistant Examiner* — David B Frederiksen
(74) *Attorney, Agent, or Firm* — Fish IP Law, LLP

(57) ABSTRACT

There is disclosed an apparatus is disclosed for monitoring blood coagulation comprising a main body; a test chamber for receiving a fluid sample; and a rotor disposed within the test chamber. The rotor comprises a buoyancy chamber for reducing the apparent weight of the rotor when fluid is positioned within the test chamber.

25 Claims, 8 Drawing Sheets

(56) References Cited

U.S. PATENT DOCUMENTS

| | | | | |
|---|---|---|---|---|
| 2003/0193198 A1* | 10/2003 | Wobben | ............... | F03B 13/264 |
| | | | | 290/54 |
| 2004/0131500 A1* | 7/2004 | Chow | ................... | G01N 11/14 |
| | | | | 422/72 |
| 2006/0192387 A1* | 8/2006 | Fielder | ................ | F03B 17/061 |
| | | | | 290/1 R |
| 2008/0085158 A1* | 4/2008 | Henderson | ............. | F03B 17/04 |
| | | | | 405/78 |
| 2010/0025998 A1* | 2/2010 | Williams | ............... | F03B 3/126 |
| | | | | 290/52 |
| 2013/0045852 A1* | 2/2013 | Chapman | .............. | B01D 21/26 |
| | | | | 494/10 |
| 2013/0192349 A1* | 8/2013 | Ramkumar | ......... | G01N 29/022 |
| | | | | 73/54.41 |
| 2014/0342391 A1* | 11/2014 | Kim | ............... | G01N 35/00069 |
| | | | | 435/29 |
| 2015/0160111 A1 | 6/2015 | Lewis et al. | | |
| 2015/0226725 A1* | 8/2015 | Gill | ....................... | G01N 33/49 |
| | | | | 73/64.41 |
| 2016/0116491 A1* | 4/2016 | Inoue | ................... | G01N 21/41 |
| | | | | 436/69 |

FOREIGN PATENT DOCUMENTS

| | | |
|---|---|---|
| SU | 473934 | 6/1975 |
| SU | 832422 | 5/1981 |
| SU | 842490 | 7/1981 |
| SU | 1195975 | 6/1986 |
| WO | 90/10213 | 9/1990 |
| WO | 2006/125057 | 11/2006 |
| WO | WO2016/046565 A2 | 3/2016 |

\* cited by examiner

APPARATUS FOR MONITORING BLOOD COAGULATION

This invention relates to an apparatus, in particular, but not exclusively an apparatus for monitoring the coagulation of blood of people in trauma, illness or during operations.

The terms blood 'coagulation' and blood 'clotting' are used interchangeably herein.

Blood coagulation is the change in state of blood from a liquid, to a semi-solid gel. The process requires the interaction of 3 key components i) the cells within the blood, primarily platelets but also white cells, ii) soluble proteins within the blood and iii) exposed tissue when blood vessels are injured.

Blood coagulation is initiated when the blood vessel wall is damaged exposing underlying tissue, collagen, which activates resting platelets circulating in the blood.

The platelets in turn release chemical activators which start a chain of enzymic reactions which produce a high concentration of thrombin which converts soluble fibrinogen to fibrin.

A clot is formed when the soluble blood protein fibrinogen is converted by the enzyme thrombin to insoluble fibrin. Fibrin then forms long threads which become cross-linked and bind to the remains of the activated platelets to form a mesh reinforced, flexible, elastic plug structure.

A second enzymic chain reaction (called lysis) occurs simultaneously to the first enzymic chain reaction which produces plasmin which slowly digests clots.

Therefore, there are multiple stages in the blood coagulation process where abnormalities can occur. In a bleeding or a severe haemorrhage situation, for example following a trauma, it is clinically useful to assess the state of coagulation.

It is known that the use of blood coagulation test systems determine the clotting profile which can be a graph displaying the rate of clot strength changes during the patients clotting process (time against strength). However, such systems are usually bulky and heavy scientific laboratory style instruments, making them impractical for mobile use at the point of care or the site of an accident. Currently available systems are mechanically driven directly, for example through metal wire spring linkages. This mechanical arrangement has a detrimental consequence on the achievable sensitivities and accuracy of the blood coagulation measurements due to external shocks, vibration and mechanical interference. The systems usually have an open cup for receiving the blood sample (which is the test chamber) and a movable rotor suspended within the blood. The cup and rotor move relative to each other in an oscillating motion through a predetermined angular range whereby the movement is initiated from either the cup or the rotor. Changes in the rotational resistance are used to determine the changing clot strength in the coagulating blood. These changes are plotted on a trace to produce a graphical representation of the progress of the performance of the clotting blood. Therefore, any vibrations transmitted from the drive mechanics can cause errors associated with this measurement.

The sensitivity of the measurements have been improved by using soft drive systems that exploit a magnetic drive assembly to move the rotor in the test fluid, which minimises the interference from external vibrations and shock. However, frictional forces of the bearings and the drive system of the rotor and the container are usually present which continues to provide a significant interference contribution, thereby having a detrimental effect to the sensitivity of the device.

Blood starts the clotting process immediately it is out of the body's blood vascular system. Therefore, if the blood sample needs to be transported to the location of the analyser the blood will have started the coagulation process. In practice anticoagulants are used to preserve the sample as a free moving un-clotted liquid state. Before charging the sample into the laboratory style analyser the anti-clotting process must have an antidote applied to allow the blood sample to restart its clotting process. This process of preventing the clotting process by the introduction of chemicals then reactivating the clotting process by the introduction of further, but different chemicals is extremely vulnerable to inaccuracies and human error.

There is also a need to provide a blood coagulation monitoring apparatus that can be used in the testing of the effect of non-vitamin K oral anticoagulant drugs. Whilst the apparatus may be used by the drugs companies in pre-trials, there is also a requirement for a suitable method to enable doctors to monitor and ensure their patients are following the treatment regime correctly, so as to prevent over dosing or under dosing which could be perceived as being dangerous to the patient. Therefore, it is envisaged that these devices will be required in doctors' surgeries, clinics and laboratories throughout the world.

Therefore, the present invention and its embodiments are intended to address at least some of the above described problems and desires. In particular to provide a portable, robust and stable apparatus for providing real time information on the blood coagulation of fresh blood of a patient, whereby the results have an improved sensitivity, quality and reliability.

According to a first aspect of the invention there is provided an apparatus for monitoring blood coagulation comprising:
 a main body;
 a test chamber for receiving a fluid sample; and
 a rotor disposed within the test chamber,
  wherein the rotor comprises a buoyancy chamber for reducing the apparent weight of the rotor when fluid is arranged within the test chamber.

The rotor may be untethered. This means that external shocks and frictional forces may be minimised.

The rotor may be rotatable about a substantially constant pivot point. Again this reduces the energy loss associated with frictional forces since the position of the pivot point remains fixed.

The rotor may have a base unit having a bearing with a domed tip and arranged such that the tip is in contact with a base portion of the test chamber to provide a lower pivot point. The domed tip minimises the contact surface area which also minimises frictional forces.

The domed tip of the bearing may have a 'ball bearing like' surface. Also the domed tip has a polished surface. Both of these features further contribute to reducing frictional forces associated with the motion of the rotor about its pivot point.

The base portion 12 of the test chamber may comprise a receptacle having a trough for receiving the domed tip of the bearing. The receptacle helps to ensure that the position of the pivot point remains substantially fixed. The trough is arranged to compliment the domed tip of the bearing so as to minimise frictional forces.

At least part of the surface of the receptacle may have a polished surface. As per the domed tip, this is to make the contact point in the trough as smooth as possible so as to minimise the frictional forces.

The rotor may comprise a first portion and a second portion configurable to create an internal space there-between. Alternatively, a space may be provided in a single integral portion if desired.

The first portion and the second portion may be adhered together. This ensures that the first portion and second portion remain attached together and in co-operably arranged so as to maintain the space formed there-between.

The internal space may comprise an inert gas. The inert gas provides a buoyancy effect of the rotor, thereby reducing the frictional forces experienced at the lower pivot point.

Alternatively, the internal space may comprise air. The air provides a buoyancy effect of the rotor, thereby reducing the frictional forces experienced at the lower pivot point.

The main body and the test chamber may form a capsule. This is a portable arrangement that can be dispatched to the point of incident.

The apparatus may further comprise an analyser. This enables monitoring of the blood at a remote site.

The analyser may comprise a port for receiving at least part of the capsule. This enables the capsule to be removably attachable to the analyser, enabling further testing on subsequent capsules for holding different blood samples to be applied by the analyser.

The apparatus may further comprise a magnetic drive system. This will reduce noise effects caused when direct, mechanical drive systems are applied.

The magnetic drive system may comprise a driver magnet and a follower magnet arrangement, the follower magnet being movable between a first position and a second position in response to the magnetic field of the driver magnet. This magnetic drive system enables indirect drive of the rotor within the test chamber, thereby improving sensitivity of measurements by eliminating, or at least minimising interference caused by external shocks, vibration and mechanical interference.

The driver magnet may be located external to the test chamber. This prevents the need for the driver magnet to be located within the capsule, making the disposable capsules cheaper to manufacture.

The follower magnet may be located on or in the rotor. This ensures that as the movement of follower magnet is influenced by the changing magnetic field, so too is the movement of the rotor i.e. the rotor is caused to rotate.

The driver magnet may be movable for varying the magnetic field incident upon the follower magnet. This therefore causes movement of the follower magnet and hence the rotor as desired.

The drive and follower magnets are magnetically attracted to each other. This therefore magnetically pulls the follower magnet towards the driver magnet so that the follower magnet moves in the direction of motion of the driver magnet.

Alternatively, the drive and follower magnets are magnetically repelled to each other. This therefore magnetically pushes the follower magnet away from the driver magnet so that the follower magnet moves in the direction of motion of the driver magnet.

The follower magnet may be reciprocally movable long an arcuate path.

Beneficially, the apparatus may be portable. This enables the apparatus to be transported to the patient, even at remote sites, enabling the blood to be monitored in real time.

In an alternative embodiment of the invention there is provided a method of monitoring the coagulation of blood using the above-mentioned apparatus, the method comprising the steps in no particular order of:
 a) disposing a fluid sample within the test chamber;
 b) providing an upward force on the rotor by means of the buoyancy chamber; and
 c) reducing the apparent weight of the rotor.

The test chamber and main body may form a capsule and the method may further comprise inserting the capsule into a port of an analyser.

Alternative methods of enabling cooperation between the analyser and the capsule may be applied if desired.

Subsequent to insertion of the capsule into the port of the analyser, the capsule may complete a pre-calibration procedure. This means that a pre-calibration can be applied prior to use of the apparatus on the blood of a patient. This minimises the time required to fully calibrate the apparatus prior to the test commencing at the point of care or site of the accident.

The pre-calibration process may be carried out on air within the capsule. This provides a suitable calibration relating to the apparatus itself prior to the insertion of a blood sample into the test chamber.

Subsequently to the fluid being disposed in the test chamber, the calibration process may be commenced until full calibration of the apparatus is obtained. This minimises the time of full calibration prior to use of the apparatus at the point of care or site of an accident.

The method may further comprise:
 activating the magnetic drive system and moving the rotor reciprocally about an arcuate path.

The method may further comprise monitoring the reciprocal movement of the rotor so as to determine the resistive property of the test fluid.

In a further embodiment of the invention, there is provided a test capsule for use with a port in an analyser, the capsule comprising
 a test chamber for receiving a fluid sample; and
 a rotor disposed within the test chamber,
 wherein the rotor comprises a buoyancy chamber for reducing the apparent weight of the rotor when fluid is arranged within the chamber.

In a further embodiment of the invention there is provided a blood coagulation analyser comprising:
 a main housing having a port located therein and an abovementioned test capsule receivable within the port, the test capsule for receiving the blood sample to be analysed.

Whilst the invention has been described above it extends to any inventive combination of the features set out above, or in the following description, drawings or claims. For example, any features described in relation to any one aspect of the invention is understood to be disclosed also in relation to any other aspect of the invention.

The invention will now be described, by way of example only, with reference to the accompanying drawings, in which:

FIG. 2b is a top view of the capsule of FIG. 2a;

Figure 1:
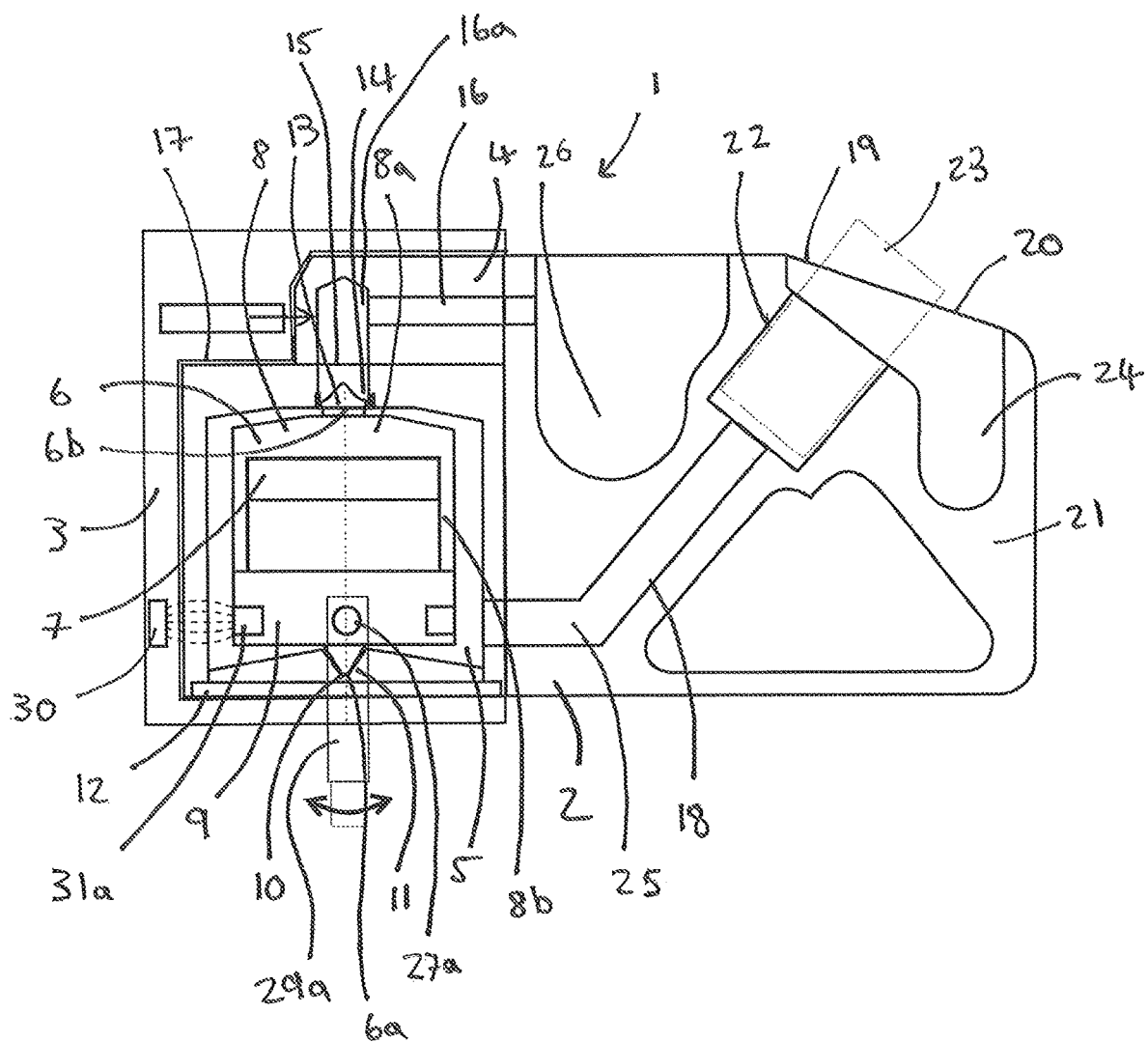
FIG. 1 is a cross sectional view of the apparatus in accordance with an embodiment of the present invention.
Figure 2A:
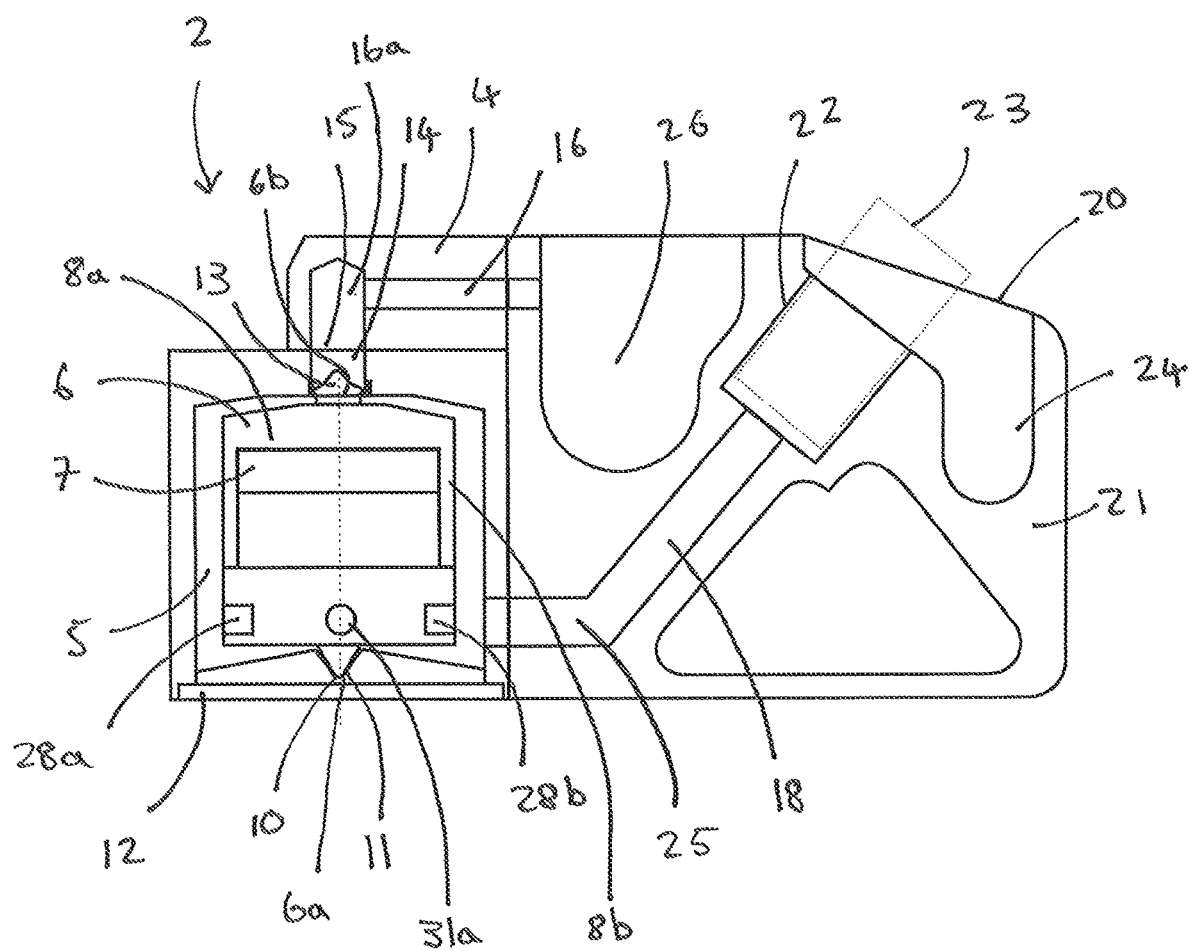
FIG. 2a is a cross sectional view of a capsule of the invention of FIG. 1.
Figure 2B:
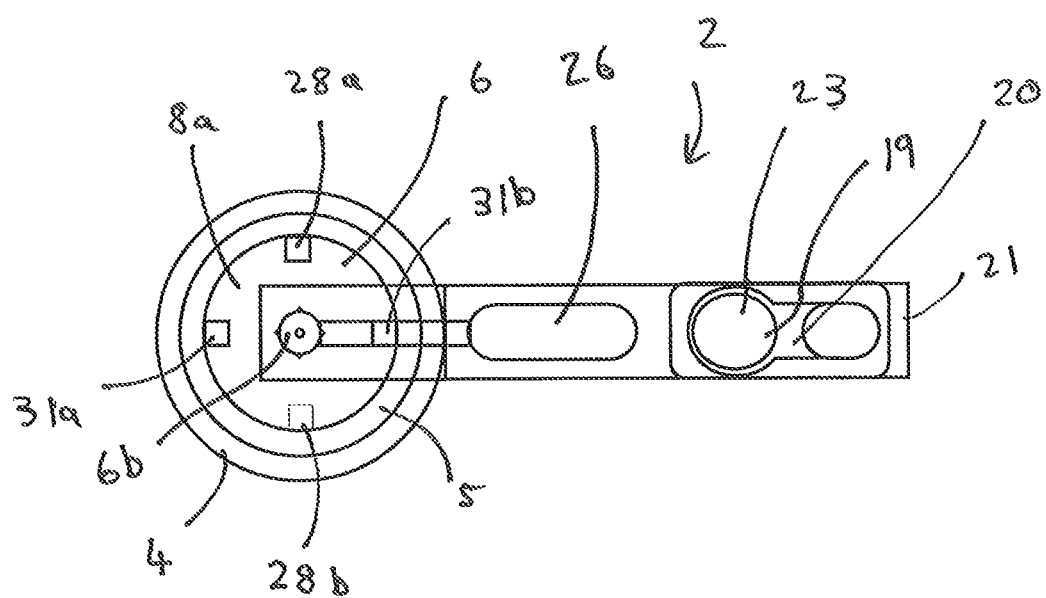
Figure 3:
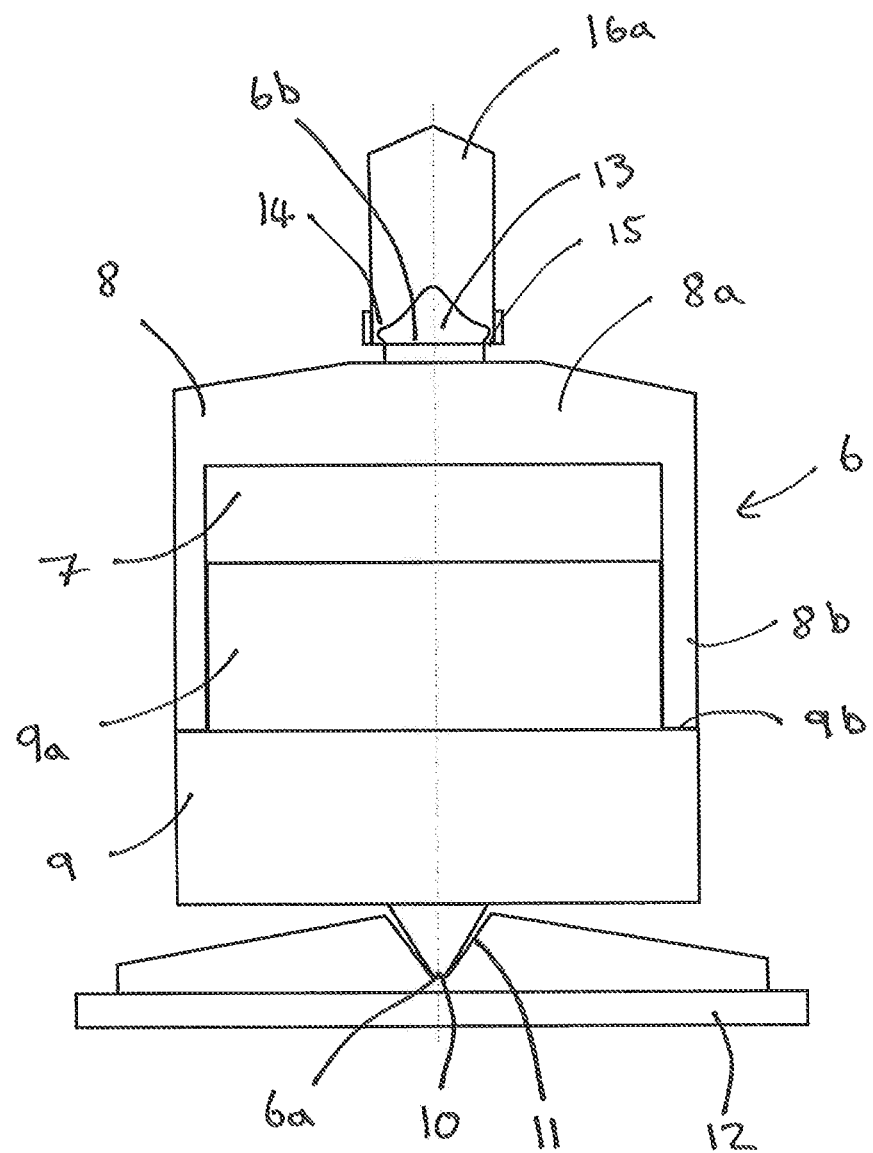
FIG. 3a is a side view of the rotor and bearings of FIG. 1.
FIG. 3b is a side view of a rotor and bearing of an apparatus according to a further embodiment of the present invention.

Referring firstly to FIG. 1 there is shown an apparatus 1 for monitoring blood coagulation, comprising a capsule 2 and an analyser 3. The capsule 2 as shown in FIGS. 2a and 2b comprises a main body 4 and a test chamber 5 positioned within the main body 4 at a front end. Test fluid is positionable within the test chamber 5. A rotor 6 is disposed within the test chamber 5, such that it is movable about the longitudinal axis of the test chamber 5, which corresponds to its vertical axis. The rotor 6 is arranged to be free spinning within the test chamber 5. The rotor 6 comprises a buoyancy chamber 7 for reducing the apparent weight of the rotor 6 when the test fluid is applied within the chamber 5. The buoyancy chamber 7 comprises an internal space formed between a first portion 8 and a second portion 9 of the rotor 6. The space is filled with air that is trapped as the first portion 8 and second portion 9 are brought together and secured by application of an adhesive at the joint. As shown in FIG. 3, the first portion 8 has an upper circular disc 8a and a wall 8b extending downwardly from the peripheral edge of the circular disc 8a for forming a female part of the rotor 6. The second portion 9 comprises a 'top hat' portion having a central region 9a and a rim 9b, whereby the central region 9a is the male part that fits within the female part of the rotor 6. The height of the walls 8b of the female part is greater than the height of the central region 9a that extends from the rim 9b of the second portion 9. This therefore provides the space forming the buoyancy chamber 7. The second portion 9 is configured to fit securely within the first portion 8 such that the ends of the wall 8b come into contact with the rim 9b of the second portion 9 and the inclusion of an adhesive at the contact region ensures the first and second portions 8,9 remain secured together.

Without limiting to a particular scientific conjecture or theory, the buoyancy chamber 7 provides an upward force on the rotor 6 when it is fully or partially immersed in the test fluid, in accordance with Archimedes principle whereby the magnitude of the buoyant force on the rotor 6 is equal to the weight of the fluid it displaces. This arises because the air is less dense than the test fluid giving a relative density of $\rho'=\rho_{rotor}-\rho_{fluid}$. The resulting upward force alters the apparent weight of the rotor 6 whilst the mass of the object doesn't change it is perceived to be lighter in such circumstances.

The buoyancy force is dependent on the density of the test fluid, the volume of the fluid displaced and the local acceleration due to gravity and it is necessary to choose these parameters depending on the fluid to be tested. This is necessary since it is desirable to have a positive weight associated with the rotor so that it may move as required to monitor the resistance caused by the fluid.

As shown in FIG. 3a bearing 10 having a conical shape with a domed tip 10a is located at the base of the second portion 9 of the rotor 6. The tip 10a of the bearing comprises a highly polished surface and the side walls of the bearing diverge along a linear path, away from the domed tip 10a to a base 10b of the bearing, which is positioned to extend adjacent the base of the second portion 9.

The domed tip 10a of the bearing 10 is receivable in a receptacle 11 located in a base portion 12 of the main housing 4 so as to provide the lower pivot point 6a of the rotor 6 in the test chamber 5. A face of the domed tip 10 makes contact and is located and supported by a trough region 11a of the receptacle 11. The trough 11a of the receptacle 11 is contoured and polished to complement the shape and diameter of the domed tip 10a of the bearing 10.

This contoured feature and the fact that both the domed tip 10 of the bearing and the polished trough 11a of the receptacle 11 have only tiny contact surface areas contributes to minimising any mechanical interference and the frictional forces at the contact point. Reducing the apparent weight of the rotor 6 is beneficial in minimising the frictional forces generated at the lower pivot point 6a and leads to highly sensitive measurements being obtained.

The rotor 6 is centralised within the test chamber 5 between the lower pivot point 6a, which has already been described and an upper pivot bearing defining an upper pivot point 6b. These pivot points remain substantially constant on rotation of the rotor 6 however the rotor 6 is not tethered to these pivot points.

The upper pivot point 6b extends from the top of the first portion 8 of the rotor 6 and comprises a male bearing 13 as shown in FIG. 3a that is tapered at its top end so as to be received by an aperture located in the main body 4 of the capsule 2. The male part of the bearing 13 is co-operable with a female part of the bearing 14 located on the upper wall of the test chamber 5. The female part of the bearing 14 has four apertures (not shown) positioned equidistant around the bearing 14 which provides four pathways permitting the passage of air and sample fluid from the inside of the test chamber 5 and through the ventilation aperture 15 enabling the air and sample fluid to pass into the ventilation gallery 16 disposed within the main body 4 of the capsule 2 to ensure the test chamber 5 is completely charged with blood. Therefore, the ventilation gallery 16 is only filled with test fluid when the test chamber 5 is full.

In an alternative embodiment, as illustrated in FIG. 3b of the drawings, both the lower bearing 10 and upper male bearing 13 comprise substantially the same shape. The features of the embodiment illustrated in FIG. 3b are substantially the same as the features illustrated in FIG. 3a and so like features have been referenced using the same numerals but increased by 100. The bearings 110, 113 illustrated in FIG. 3b comprise a domed tip, which is preferably polished, and side walls which diverge along an arcuate path away from domed tip 110a, 113a to a waist portion 132 disposed intermediate the tip 110a, 113a and a base of the respective bearing 110, 113. The side walls subsequently curve around the waist portion and converge beyond the waist portion toward the base of the respective bearing. The waist portion 132 thus comprises a larger diameter than the base of the bearing.

The bearings 110, 113 further comprise a plurality of notches 133 (these are only illustrated in connection with the lower bearing 110) or cutaway regions formed within the bearing at the waist portion 132, which are angularly separated around the waist portion 132. In use, the domed tip 110a, 113a of each bearing 110, 113 is received within the respective receptacle 111 and female bearing 114 such that the domed tip 110a, 113a locates within the corresponding trough 111a and formation (not shown) in the female bearing 114 to centralise the rotor 106 within the test chamber 105. The waist portion 132 of each bearing helps to minimise sideways movement of the rotor while reducing friction at the interface between the bearing 110, 113 and corresponding receptacle/female bearing 111, 114. Moreover, when the test chamber 105 is charged with a test fluid, then the fluid is permitted to move into the receptacle 111a and female bearing 114 and pass beyond the waist portion 132 via the notches 133 to lubricate the interface between the bearing 110, 113 and corresponding receptacle/female bearing 111, 114 to further reduce friction at the interface.

On manufacture of the capsule 2, the male part of the upper bearing 13 is inserted within the corresponding female part of the bearing 14 enabling fluid communication between the test chamber 5 and the ventilation gallery 16. The base cap 12 of the main body 4 is then applied and adhered to the base of the main body 4 to secure the rotor 6 into position. An analyser 3 is used to monitor the movement of the rotor 6 in the sample filled test chamber 5.

At least part of the capsule 2 is receivable in a port 17 of the analyser 3 and the capsule 2 is removable from the analyser 3 once the test has been completed. Therefore, the capsule 2 is single use and disposable. The capsule 2 is completely sealed prior to use.

The capsule 2 has a feeder channel or feeder gallery 18 via which the test fluid is to be inserted into the test chamber 5. The inlet 19 of the feeder channel 18 can be initially terminated by a cover membrane 20 which is penetrable by the tip of a standard medical syringe. The cover 20 ensures no contamination enters the capsule 2 before charging with a sample.

As shown in FIGS. 1, 2a, 2b and 5, the main body 4 of the capsule 2 comprises a handle 21 with a sample charging tapered orifice known as a luer fitting 22. The luer fitting 22 will accept the luer discharge tip 23 of a standard medical syringe. An overflow reservoir 24 is included adjacent the inlet 19. Connected to the inlet 19 is a feeder leading into a lower channel 25 that charges the test chamber 5 with a blood sample. At the top of the test chamber 5 is the ventilation aperture 15 leading to a short ventilation gallery 16a comprising a vertical shaft leading to the upper substantially horizontal channel 16 that acts as a test chamber ventilator and feeds an overflow reservoir 26.

Figure 4A:
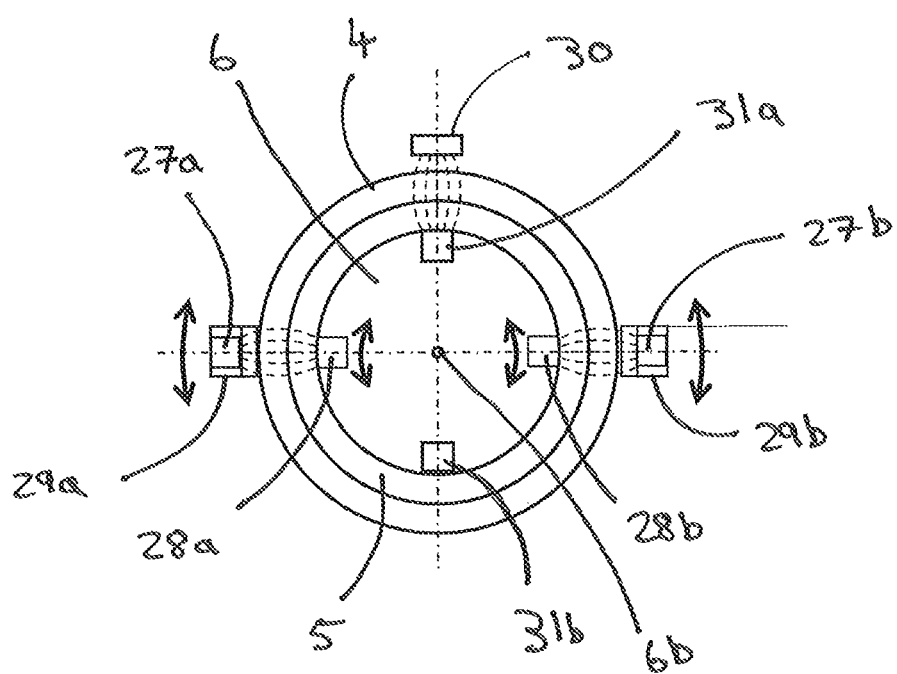
FIG. 4a is a top view of a schematic of the rotor and chamber of FIG. 1.
Figure 4B:
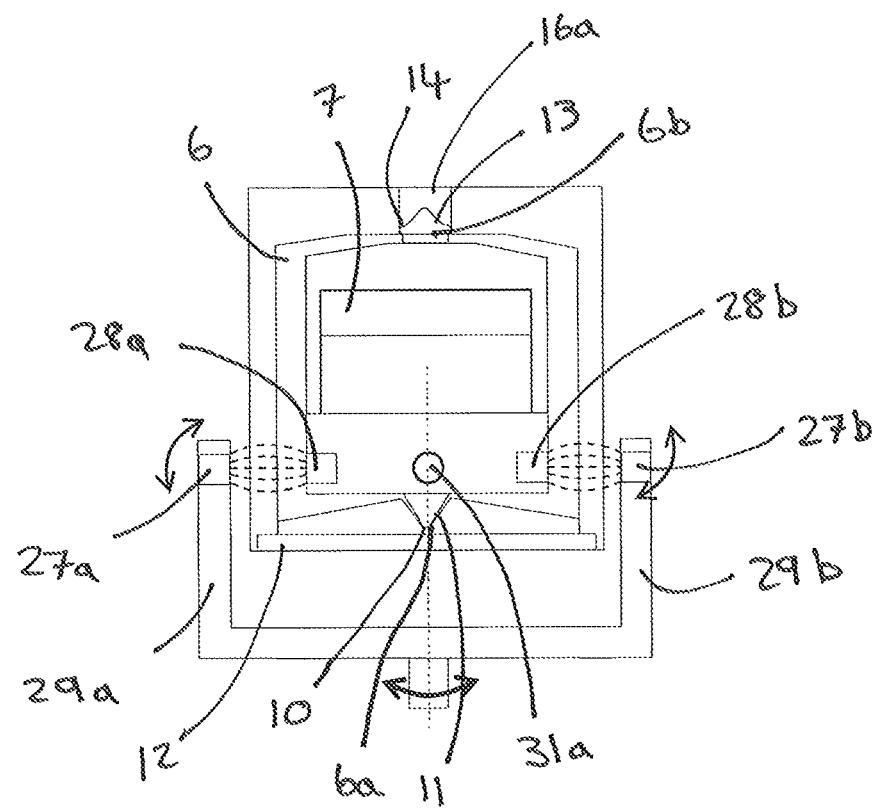
FIG. 4b is a side view of a schematic of the rotor and chamber of FIG. 1.

The apparatus incorporates a soft drive system as shown in FIG. 1, FIG. 4a and FIG. 4b, for example a magnetic drive system. The magnetic drive system comprises a drive magnet 27 and a follower magnet 28 arrangement, the follower magnet 28 being incorporated in the rotor 6 and movable in the test chamber 5 between a first position and a second position in response to the reciprocally swinging magnetic field of the drive magnet 27.

In FIGS. 4a and 4b there is shown a first and second drive magnet 27a, 27b positioned at opposing sides of the apparatus holding port 17 comprising a receiving chamber located in the housing of the of the analyser 3. The first and second drive magnets 27a, 27b are located on a first and second movable arms 29a, 29b respectively. The first and second arms 29a, 29b are linked together as shown in FIG. 4b. Therefore, the first driver magnet and second driver magnets 27a, 27b are positioned outside of the test chamber 5 and outside the main body 4 of the capsule 2. The arms of the arm assembly 29 are caused to move back and forth by a cam and stepper motor arrangement (not shown) which is located within the housing of the analyser 3. The range of movement of the arms 29a, 29b is predetermined to be 4.45°.

The first and second follower magnets 28a, 28b are located in opposing sides of the rotor 6. The respective drive magnets 27a, 27b and follower magnets 28a, 28b are attracted to each other such that movement of the drive magnets 27a, 27b causes movement of the follower magnets 28a, 28b. The movement of both drive and follower magnets is along an arcuate path and is a reciprocal movement. As the follower magnets 28a, 28b are incorporated in the rotor 6, the rotor 6 will move in the same arcuate path and reciprocal movement of the rotor 6 with the follower magnets 28a, 28b is provided.

A magnetic field detector 30 is located within the housing of the analyser 3 for detecting the change in the magnetic field of a sensor magnet 31a which is arranged 90 degrees out of phase to the follower magnets 28a, 28b. A further sensor magnet 31b is also arranged on the opposing side of the rotor 6 (i.e. opposite the first sensor magnet 31a) to ensure the rotor 6 has perfect balance. This further magnet 31b is redundant as a sensor magnet unless the rotor becomes rotated by 180° on insertion of the capsule 2 into the capsule port 17. This makes the insertion of the capsule 2 within the analyser 3 simple and means it does not require any pre-setting of the rotor 4 or significant thought process by the user. As the capsule 2 is inserted into the port 17 the rotor 6 will automatically orient into one of the four options to operate.

Since the two driver magnets 27a, 27b and two sensor magnets 31a, 31b are relatively heavy they are positioned towards the base of the rotor 6 to ensure it has maximum stability by keeping the complete rotor 6 centre of gravity as low as possible.

The movement of the swing arms 29a, 29b with their respective drive magnets 27a, 27b causes movement of the rotor 6 within the test chamber 2. At initial charging of the blood sample the rotor has a maximum range of movement being drawn by the drive magnets 27a, 27b, however as the blood sample coagulates the range of movement of the rotor 6 is changed as the resistive forces of the clotting sample varies. These changes are detected by the magnetic field detector 30 as the field of the sensor magnet 31a oscillates past it.

The apparatus 1 will detect both clotting, strengthening and lysis (which is the weakening of the clot). The capsule 2 is made from polycarbonate which is a commonly available industrial and medical plastic, and has many desirable properties. For example polycarbonate is good for machining and for being glued together. It is proven to be stable over time, is semi opaque, inert to the medical chemicals being applied during manufacture and clinical use and does not contribute to the biological and chemical reaction of blood coagulation.

In use, a health care professional inserts the capsule 2 into the port 17 of the analyser 3. The analyser 3 detects the presence of the capsule 2 and automatically warms up the test chamber 5 to the required test temperature and is ready in minutes to receive the sample of blood from the patient. The default temperature is 37° C. but this temperature can be programmed to another temperature and is set by the operator. Operating the apparatus 1 at a higher temperature than 37° C. is desirable if the casualty has experienced hyperthermia, an acute temperature elevation caused by exposure to excessive heat, or combination of heat and humidity, that overwhelms the heat-regulating mechanisms of the body. Operating the apparatus 1 at a lower temperature than 37° C. is desirable if the casualty has experienced hypothermia, a condition in which the body's core temperature drops below that required for normal metabolism and body functions.

At start-up a pre-calibration procedure is performed such that the apparatus 1 reaches between 80%-90% of its full calibration status. This process is carried out with air in the test chamber 5 that was trapped therein when the capsule 2 was sealed at manufacture. The pre-calibration procedure is carried out with the full system in operation. Once completed the pre-calibration process is terminated. To start the coagulation profile analysis, a fresh blood sample is applied via the luer fitting 22 using a standard medical syringe (without a needle). The tip of the syringe 23 is used to rupture and break open the sealing membrane 20 covering the capsule entry and spill reservoir 24. The syringe tip 23 then enters the luer fitting 22. When the syringe tip 23 is securely fitted in the female luer fitting 22 the blood sample is injected into the feeder channel 18 and then the lower channel 25 subsequently entering the test chamber 5 where the blood is disposed. On insertion of the blood sample the buoyancy chamber 7 provides an upwards force on the rotor 6 and the apparent weight of the rotor 6 is reduced. The full calibration process is then commenced until full calibration of the apparatus is obtained. By using a pre-calibration process before insertion of the blood, sample calibration takes a fraction of the time compared to other known instruments and this can therefore provide a speedier and more reliable result.

To ensure the test chamber 5 is always fully charged the volume of the blood sample applied exceeds the volume of the test chamber 5 in the capsule 2. Excess blood will escape through the ventilator aperture 15 and exit through the ventilation gallery 16 into the overflow reservoir 26.

An audio alarm and/or other indicator will be activated informing the health care professional that the test chamber 5 is full, however a significant variation in the thumb resistance on the syringe will also be experienced by the healthcare professional after the air has been expelled from the test chamber 5 and the thicker blood is then forced through the apertures 14 of the bearing and through the ventilation aperture 15.

Once the full calibration procedure has been completed, the apparatus initiates test mode automatically. When operating, the motor in the analyser causes movement of the arms 29a, 29b back and forth. The drive magnets 27a, 27b located on the movable arms 29a, 29b also move back and forth. Since the follower magnets 28a, 28b are magnetically attracted to the drive magnets 27a, 27b they are also caused to move resulting in a reciprocal movement of the rotor 6 about an arcuate path. Initially the range of movement of the rotor 6 and follower magnets 28a, 28b is synchronised with that of the driver magnets 27a, 27b. On charging of the test chamber 5 the blood sample is unclotted. The resistance provided by the unclotted blood is insufficient to overcome the magnetic attraction between the driver magnets 27a, 27b and follower magnets 28a, 28b. However, after a period of time, the blood sample becomes thicker and progressively clots. As the blood sample progressively clots the rotor 6 then experiences more resistance to movement and the range of the rotor 6 is reduced. The magnetic field detector 30 monitors the magnetic field of the sensor magnet 31a over time and therefore can provide the information for enabling a graphical representation of the blood coagulation profile to be produced.

It is quick to prepare the apparatus for a further test, whereby the capsule 2 that has completed testing is removed from the analyser 3, disposed of and a fresh capsule 2 is inserted ready for the next patient blood analysis. If the analyser 3 is contaminated by blood smear or spillage the analyser casing can be wiped over with a cleansing and sterilising solution.

The apparatus 1 is much smaller than standard Laboratory style test instruments and is light enough to be carried by a single person. Therefore, it is a portable apparatus that can be applied and operated at any site. Further it can start and continue analysis while mobile without the need for a mains power supply since it has an internal energy source e.g. battery arrangement (not shown). This also enables the blood coagulation results to be obtained in real time, even at remote trauma sites. This battery powered and portable characteristic also makes the apparatus suitable for third world countries where there is not always a reliable supply of mains electricity.

Very rapid results may also be provided due to the pre-calibration process, whereby pre-calibration is carried out on an empty capsule i.e. a capsule with air rather than a blood sample providing an initial calibration status of 80% to 90%. Then once the capsule has been filled with the test sample the final 20% to 10% of the calibration procedure can be implemented. The duration of this final calibration stage can be few seconds, rather than a many minutes for a full calibration as per known instruments. This clearly offers greater response time allowing for the apparatus to be applied to the patient within a matter of seconds.

As the patient sample can be tested in the analyser at the point of care, location of an accident, the site of trauma, or during transit of the patient, valuable real time results will be available to a clinician, for example the first results may be obtained after approximately three minutes depending on the reaction time of clotting. When you compare this to the delay caused by a patient sample being taken to the location of a Laboratory style instrument and analysed by specialist scientific staff which is often one and a half hours, this is a significant improvement.

The capsule 2 may also be marked with an identifier which may be a traceable bar code or an electronic tag as desired, whereby all information regarding the traceability of the capsule 2 is recorded without the input of the records by an operator. This reduces the possibility of human error and allows the medical practitioner to apply their duties to a function of a higher priority. When the capsule 2 is inserted into the analyser 3 the identifier is read and recorded automatically by the analyser 3. When a fresh empty capsule 2 is inserted in the port of the analyser, a detector (not shown) can read, de-code and record the data and initiate pre-calibration of the individual capsule 2. The bar code label is printed on a clear self-adhesive membrane. The capsule bar code label is positioned so that when the test chamber is full the red blood will be observed by the barcode reader through the clear label and introduce an apparent change in code. When read, this change indicates the capsule 2 is full so the operator is instructed by the analyser screen (not shown) or an audio warning to stop inserting blood and the test automatically starts.

The apparatus has a standby function for conserving any energy in the power storage device e.g. battery, contained therein and enabling a quick start up procedure where necessary. Therefore, there is no requirement for external switches or buttons since there is no need to switch the apparatus on or off. A docking station (not shown) is provided as a home location of the apparatus when the apparatus is not being used in mobile operation. The docking station is a housing cradle which is connected to a standard mains electricity supply and will provide a low voltage trickle charge to the internal batteries of the apparatus and also provide a communication base to upload stored results to a PC or the hospital communication network by direct cable connection, optical communication transmitter and receiver, Bluetooth or WiFi.

The apparatus 1 has a variety of user interfaces for example includes a touch screen (not shown) for entering information about the patient, viewing preliminary graphical representations of the device and selecting transfer of information of the test sample to a remote location. An overflow alert mechanism and alarm selector (not shown) is also included on a screen located on the analyser. It also has computational capabilities and a memory storage area for storing a results library to which the monitored output may be compared. There is also a built in external magnetic detector and magnetic compensators for dealing with the changes to the direction of the apparatus within the Earth's magnetic field and other influential magnetic fields.

The capsule 2 is a sealed device that can be used in both sterile and non-sterile environments, for example wards, road ambulances, air ambulances and even at a scene of an accident or at a remote site. Consequently the initial sample can be taken from the patient, at the very earliest opportunity by a medic or paramedic. The apparatus 1 can then be transported with the patient and will provide a continually, upgraded report of the real time changes in the clotting status during its natural clotting progression. This can therefore help them to introduce appropriate interventions to control bleeding in a timely manner.

There are many parts of the world where the electricity supply is unreliable, therefore this apparatus 1 is a significant advantage in these areas since it has the ability to continue testing in the event the main power system is interrupted. For example the apparatus 1 may be automatically operated via a battery or in a further embodiment of the invention the apparatus 1 has an automatic battery intervention procedure for connecting the motor to the battery. In the event that the batteries are discharged below a predetermined limit the unit will automatically move into hibernation mode to protect the systems and save recorded data so that recharging can commence without any intervention or active maintenance by simply replacing the apparatus in the docking station.

The apparatus 1 can be used on fresh blood because the analyser and capsule by their mobile characteristics are available when fresh unclotted blood is available to be used. Blood starts the clotting process immediately it is out of the body's blood vascular system. Therefore if the blood sample needs to be transported to the location of the analyser the blood will have started the coagulation process. In current practice anticoagulants are used to preserve the sample as a free moving un-clotted liquid state. Before charging the sample into the laboratory style analyser the anti-clotting process must have an antidote applied to allow the blood sample to restart its clotting process. This combined process of preventing the clotting process by the introduction of chemicals then reactivating the clotting process by the introduction of further but different chemicals is extremely vulnerable to inaccuracies and human error. Therefore, the portability of the analyser removes the need to transport the blood sample over long distances meaning the coagulation can be monitored in real time without the need to use anti-coagulants and their antidotes.

Ultimately, this apparatus is advantageous because i) the interference and frictional forces on the pivot point in the test chamber are significantly minimised and as a result a more accurate and sensitive blood clotting profile is provided by increasing the proportion of the effect of the blood clotting forces compared to the ratio of interfering and frictional resistive forces, ii) the minimising of operator activity allows semi-skilled health care staff to commence the analysis, iii) the elimination of reagent usage allows the system to be operated at any time and iv) the complete portability of the device allows the system to be used in previously inaccessible locations.

Various modifications to the principles described above would suggest themselves to the skilled person. For example, alternative to air, any inert gas can be applied to the buoyancy chamber, however air is cost effective to provide and safe and does not require a further air evacuation and gas insertion process at the capsule manufacture stage.

Alternatively to a tapered male part of the bearing 13 to be used with a corresponding female part of the bearing 14, a shaft and hole may be implemented, however this provides high frictional forces that will have an adverse effect on the sensitivity of the instrument. A mushroom shaped bearing will give support but there will only be a thin line of contact which will reduce the frictional surface area of the contact region. The line contact orientation will maintain concentricity. Also the bearing need not be mushroom shaped, but may be of an alternative shape having the tapered upper surface for acting as a guide means.

Alternatively to a level indicator (not shown) of mechanical means, light can be used to observe the level of the test fluid in the test chamber or upper gallery.

Figure 5:
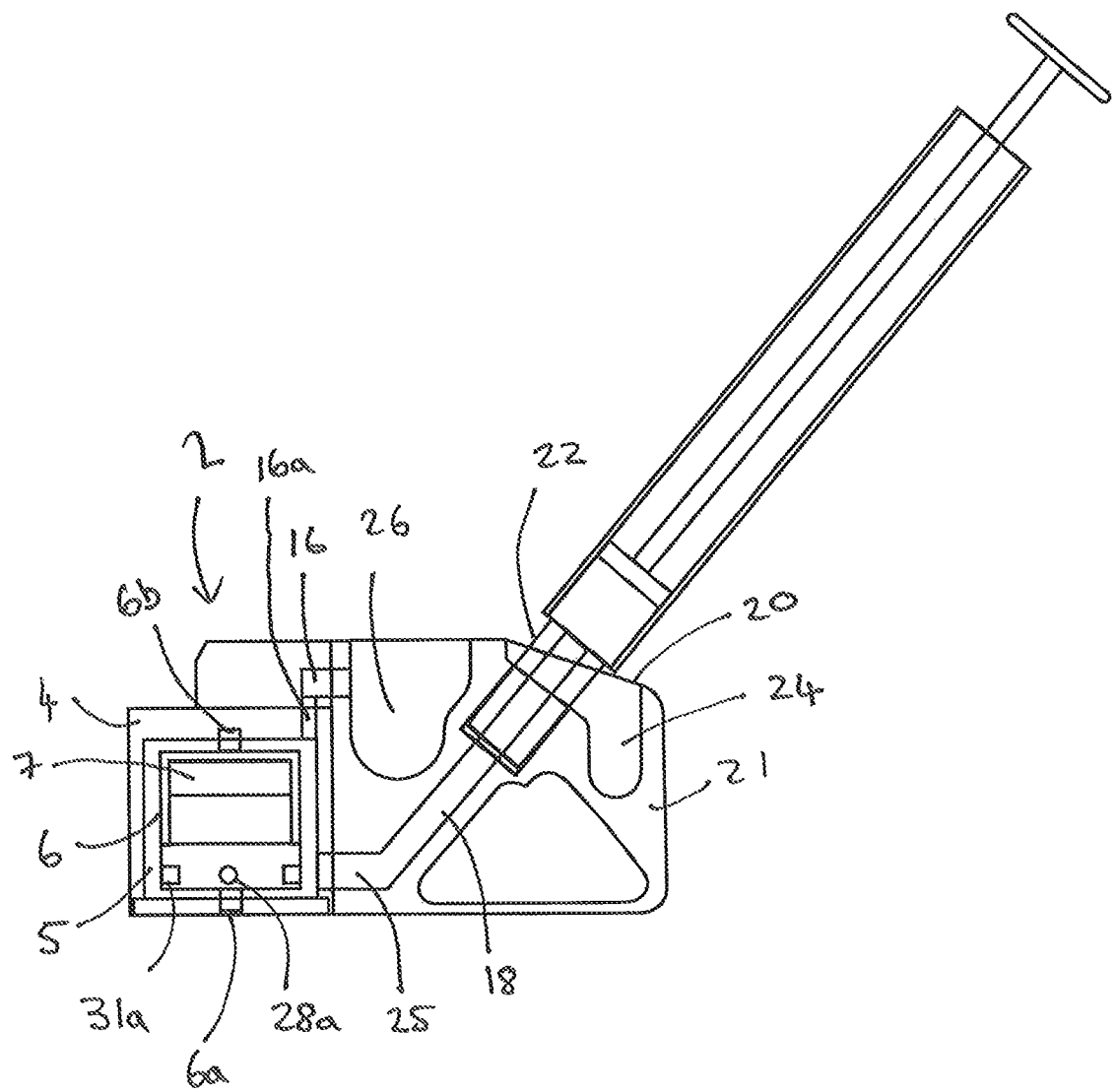
FIG. 5 is a cross sectional view of the apparatus in accordance with a second embodiment of the invention; and, FIG. 6 is a top view of a rotor and an electromagnetic drive assembly.

In FIG. 5, there is shown an alternative embodiment of the invention wherein the contact points of the rotor 6 are shafts and the overflow of blood does not pass through the mushroom bearing, but through an aperture located in the capsule adjacent to the contact point. However, the same principle of operation applies.

Alternatively, there is no pre-calibration process and full calibration commences on insertion of the blood in the container.

Alternatively to a single drive magnet, multiple drive magnets may be applied.

Instead of the follower magnets being incorporated in the rotor they may be affixed thereto.

The analysis of the blood may be terminated by the user, or alternatively the analysis may automatically terminate after a predetermined period of time, for example 90 minutes.

The test chamber may be a disposable, single use removable capsule and the handle and main body incorporating the luer may be permanently fixed component parts of the analyser. However, this arrangement may be problematic since thorough cleaning and sterilisation of the luer would be required, which is troublesome. Alternatively, the chamber may also be built into the analyser as a permanently fixed component thereof, but this again leads to problems associated with cleaning the chamber between the application of different blood samples, which may adversely lead to contamination of the subsequent blood sample.

Figure 6:
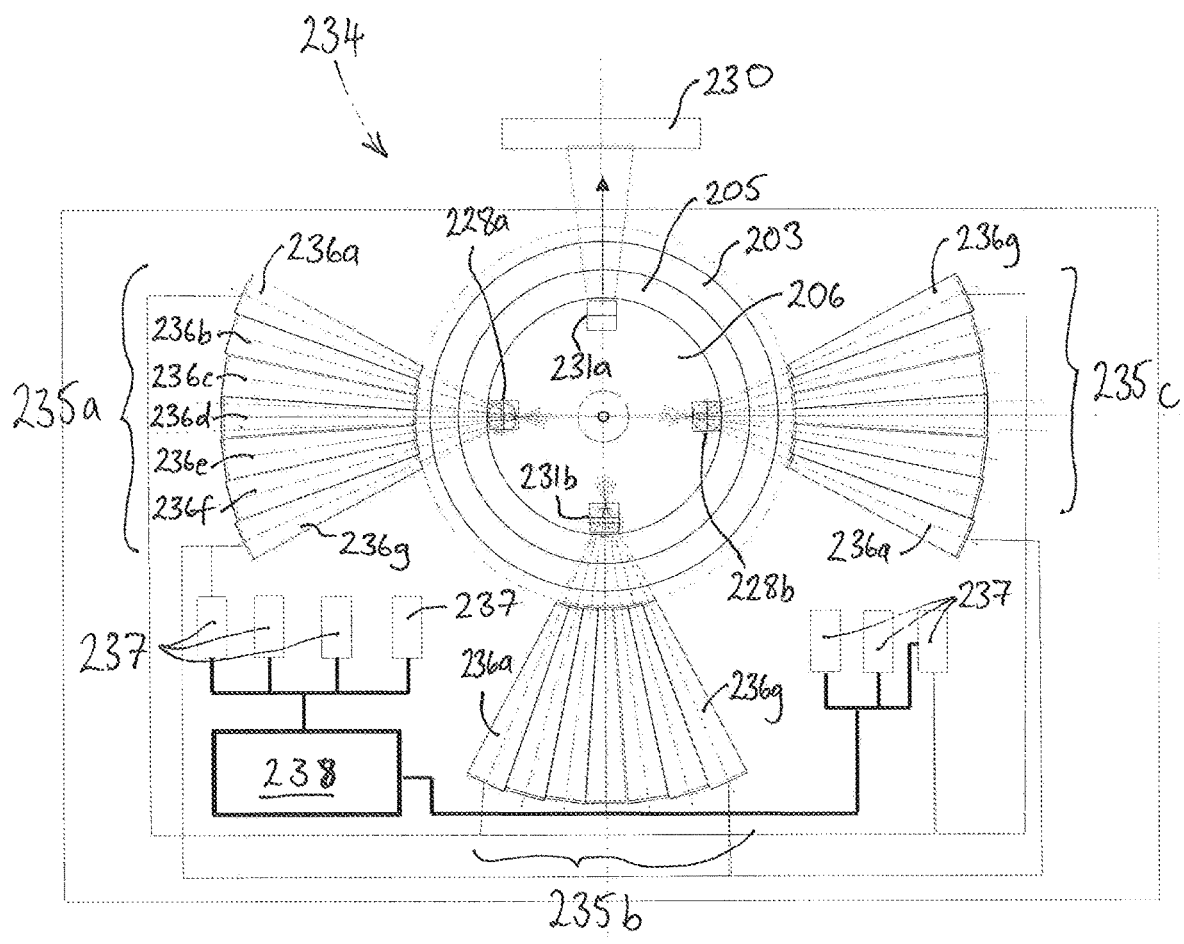

In a further embodiment, as illustrated in FIG. 6 of the drawings, the rotating arms 29a, 29b and driver magnets 27a, 27b are replaced with an electromagnetic drive assembly 234. The embodiment of the apparatus illustrated in FIG. 8 is substantially the same as the apparatus illustrated in FIG. 4a, and so like features have been referenced using the same numerals but increased by 200.

In this embodiment, the rotor 206 is driven to rotate within the chamber 205 by generating a magnetic field at a plurality of electromagnetic elements 236 which interacts with the follower magnets 228a, 228b disposed on the rotor 206. Referring to FIG. 6, the electromagnetic drive assembly 234 comprises three driver stages 235a-c angularly separated around the test chamber 205, such that a first and third stage 235a,c are arranged diametrically opposite each other with the second stage 235b angularly separated by substantially 90° from the first and third stage 235a, c. The stages 235 are orientated in substantially the same plane, which corresponds with a plane of the follower magnets 228a, 228b and each stage 235a-c comprises a plurality of electromagnetic elements 236a-f, which are separately arranged to generate a variable magnetic field.

In the illustrated embodiment, the stages 235a-c of the assembly 234 comprise seven elements 236a-g (although the skilled reader will recognise that a different number of elements may be used) and the angular separation between corresponding elements 236a-g of each stage 235 is substantially the same for each element 236a-g of the assembly 234. Corresponding elements 236a-g of each stage 235 are communicatively coupled with a common control unit 237, which is arranged to control the electrical power supplied to the respective elements 236a-g (only the first and seventh element 236a, 236g of each stage 235 is shown communicatively coupled to a control unit 237, for clarity). In this respect, the assembly 234 comprises seven control units 237, each unit 237 being arranged to control three electromagnetic elements 236, one from each stage 235.

The control units 237 are communicatively coupled to a processor 238 for timing the communication of electrical power from the control units 237 to corresponding elements 236a-g of each stage 235. Accordingly, by including a phase delay or temporal lag (for example) between the application of electrical power to each element 236a-g of a particular stage 235, it is possible to generate a spatially varying magnetic field strength along each stage of the assembly. In this manner, the magnetic field generated by each stage 235 of the assembly 234 can be used to generate both an attraction and a repulsion at the follower magnets 228a, 228b disposed on the rotor 206 and provide for a more accurate driving of the rotor 206. Moreover, the array of elements 236a-g associated with each stage 235 and the ability to temporally vary the magnetic field generated at each element 236a-g enables a number of different driving cycles to be used. For example, it is possible to generate a harmonic driving cycle, in which the magnetic field strength varies sinusoidally. Furthermore, since there is no moving parts associated with this electromagnetic drive assembly 234 compared with the rotating arms 29a, 29b, then it is anticipated that the embodiment illustrated in FIG. 6 will suffer less wear. Whilst the invention has been described above, it extends to any inventive combination of features set out above. Although illustrative embodiments of the invention are described in detail herein with reference to the accompanying drawings, it is to be understood that the invention is not limited to these precise embodiments. Furthermore, it is contemplated that a particular feature described either individually or as part of an embodiment can be combined with other individually described features, or parts of other embodiments, even if the other features and embodiments make no mention of the particular feature. Thus, the invention extends to such specific combinations not already described.

The invention claimed is:

1. An apparatus for monitoring blood coagulation comprising:
    a main body;
    a test chamber for receiving a fluid sample; and
    a rotor disposed within the test chamber centralized between a lower pivot point and an upper pivot point, but not tethered to the upper and lower pivot point,
    wherein the rotor comprises a buoyancy chamber for reducing the apparent weight of the rotor when fluid is arranged within the test chamber,
    the main body and test chamber form a capsule characterized in that the main body comprises an inlet connected to a feeder channel leading into a lower channel via which the fluid sample can be inserted into the test chamber and in that the main body further comprises, at a top of the test chamber, a ventilation aperture leading to a short ventilation gallery comprising a vertical shaft leading to an upper substantially horizontal channel via which excess fluid sample and air can exit the test chamber into an overflow reservoir.

2. The apparatus according to claim 1, wherein the rotor is untethered and/or wherein the rotor is rotatable about the upper and lower pivot points.

3. The apparatus according to claim 1, wherein the rotor has a base unit having a bearing with a domed tip and arranged such that the tip is in contact with a base portion of the test chamber to provide the lower pivot point.

4. The apparatus according to claim 3, wherein the domed tip of the bearing has a 'ball bearing like' surface or wherein the domed tip has a polished surface.

5. The apparatus according to claim 3, wherein the base portion of the test chamber comprises a receptacle for receiving the domed tip of the bearing or wherein at least part of a surface of the receptacle has a polished surface.

6. The apparatus according to claim 1, wherein the rotor comprises a first portion and a second portion configurable to create an internal space there-between.

7. The apparatus of claim 6, wherein the internal space comprises an inert gas or air.

8. The apparatus according to claim 1 claim further comprising an analyzer.

9. The apparatus of claim 8, wherein the analyzer comprises a port for receiving at least part of the capsule.

10. The apparatus according to claim 1, further comprising a magnetic drive system.

11. The apparatus according to claim 10, wherein the magnetic drive system comprises a driver magnet and a follower magnet arrangement, the follower magnet being moveable between a first position and a second position in response to a magnetic field of the driver magnet.

12. The apparatus according to claim 11, wherein the follower magnet is located on or in the rotor.

13. The apparatus according to claim 11, wherein the driver magnet is moveable for varying the magnetic field incident upon the follower magnet.

14. The apparatus according to claim 11, wherein the drive and follower magnets are magnetically attracted to each other.

15. The apparatus of claim 11, wherein the driver magnet is located external to the test chamber.

16. The apparatus of claim 11, wherein the drive and follower magnets are magnetically repelled to each other.

17. The apparatus of claim 11, wherein the follower magnet is reciprocally moveable along an arcuate path.

18. The apparatus according to claim 1, wherein the apparatus is portable.

19. A method of monitoring the coagulation of blood using the apparatus of claim 1, the method comprising the steps in no particular order of:
    disposing a fluid sample within the test chamber;
    providing an upward force on the rotor by means of the buoyancy chamber; and
    reducing the apparent weight of the rotor.

20. The method according to claim 19, wherein the method further comprises inserting the capsule into a port of an analyzer.

21. The method of claim 20, wherein subsequently to the fluid being disposed in the test chamber, a calibration process is commenced until full calibration of the apparatus is obtained.

22. The method of claim 20, wherein subsequent to insertion of the capsule into the port of the analyzer, the capsule completes a pre-calibration procedure.

23. The method of claim 22, wherein the pre-calibration procedure is carried out on air within the capsule.

24. The method according to claim 19, comprising:
activating a magnetic drive system and moving the rotor reciprocally to generate a reciprocal movement about an arcuate path.

25. The method of claim 24, comprising monitoring the reciprocal movement of the rotor so as to determine a resistive property of the test fluid.

* * * * *

UNITED STATES PATENT AND TRADEMARK OFFICE
CERTIFICATE OF CORRECTION

| | | |
|---|---|---|
| PATENT NO. | : 11,029,307 B2 | Page 1 of 1 |
| APPLICATION NO. | : 15/514356 | |
| DATED | : June 8, 2021 | |
| INVENTOR(S) | : Charles Bernard Benson | |

It is certified that error appears in the above-identified patent and that said Letters Patent is hereby corrected as shown below:

In the Claims

At Column 13, Line 60 change, "tethered to the upper and lower pivot point," to --tethered to the upper and lower pivot points,--

Signed and Sealed this
Twenty-first Day of September, 2021

Drew Hirshfeld
*Performing the Functions and Duties of the
Under Secretary of Commerce for Intellectual Property and
Director of the United States Patent and Trademark Office*